US010814352B2

(12) United States Patent
Weekamp et al.

(10) Patent No.: US 10,814,352 B2
(45) Date of Patent: Oct. 27, 2020

(54) ULTRASONIC TRANSDUCER CHIP ASSEMBLY, ULTRASOUND PROBE, ULTRASONIC IMAGING SYSTEM AND ULTRASOUND ASSEMBLY AND PROBE MANUFACTURING METHODS (71) Applicant: KONINKLIJKE PHILIPS N.V., Eindhoven (NL)

(72) Inventors: Johannes Wilhelmus Weekamp, Beek en Donk (NL); Vincent Adrianus Henneken, Utrecht (NL); Alfons Wouter Groenland, Valkenswaard (NL); Marcus Cornelis Louwerse, Nijmegen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 571 days.

(21) Appl. No.: 15/305,414

(22) PCT Filed: May 5, 2015

(86) PCT No.: PCT/EP2015/059769
§ 371 (c)(1),
(2) Date: Oct. 20, 2016

(87) PCT Pub. No.: WO2015/169771
PCT Pub. Date: Nov. 12, 2015

(65) Prior Publication Data
US 2017/0043375 A1 Feb. 16, 2017

(30) Foreign Application Priority Data

May 6, 2014 (EP) .................................... 14167101

(51) Int. Cl.
H01L 41/047 (2006.01)
B06B 1/06 (2006.01)
(Continued)

(52) U.S. Cl.
CPC .......... B06B 1/0622 (2013.01); A61B 8/4483 (2013.01); G10K 11/002 (2013.01);
(Continued)

(58) Field of Classification Search
CPC ....... B06B 1/06; B06B 1/0603; B06B 1/0607; B06B 1/0622
(Continued)

(56) References Cited

U.S. PATENT DOCUMENTS 5,329,498 A * 7/1994 Greenstein ............ B06B 1/0629
310/327
5,997,479 A 12/1999 Savord et al.
(Continued)

FOREIGN PATENT DOCUMENTS

CN 1649678 A 8/2005
CN 101344588 A 1/2009
(Continued)

OTHER PUBLICATIONS

Wodnicki, et al., "Multi-Row Linear cMUT Array Using cMUTs and Multiplexing Electronics," http://www-yg.stanford.edu/khuriyakub/opencms/Downloads/09_GE_Preprint.pdf (Abstract).
(Continued)

Primary Examiner — Derek J Rosenau (57) ABSTRACT

Disclosed is an ultrasonic transducer assembly comprising an ultrasonic transducer chip (100) having a main surface comprising a plurality of ultrasound transducer elements (112) and a plurality of first contacts (120) for connecting to said ultrasound transducer elements; a contact chip (400) having a further main surface comprising a plurality of second contacts (420); an backing member (300) comprising ultrasound absorbing and/or scattering bodies (310), said backing member comprising a first surface (302) on which the transducer chip is mounted and a second surface (306) on (Continued)

which the contact chip is mounted; and a flexible interconnect (200) extending over said backing member from the main surface to the further main surface, the flexible interconnect comprising a plurality of conductive tracks (210), each conductive track connecting one of said first contacts to a second contact. An ultrasound probe including such an assembly, an ultrasonic imaging system including such an ultrasound probes and manufacturing methods of such an assembly and probe are also disclosed.

12 Claims, 9 Drawing Sheets

(51) Int. Cl.
*G10K 11/00* (2006.01)
*A61B 8/00* (2006.01)
*H01L 41/113* (2006.01)
*H01L 41/293* (2013.01)

(52) U.S. Cl.
CPC ...... *H01L 41/0472* (2013.01); *H01L 41/1132* (2013.01); *H01L 41/293* (2013.01)

(58) Field of Classification Search
USPC ........................................ 310/322, 334, 335
See application file for complete search history.

(56) References Cited

U.S. PATENT DOCUMENTS

| | | | |
|---|---|---|---|
| 6,013,032 A | 1/2000 | Savord et al. | |
| 6,236,144 B1 | 5/2001 | Millar et al. | |
| 6,283,919 B1 | 9/2001 | Roundhill et al. | |
| 6,443,896 B1 | 9/2002 | Detmer | |
| 6,458,083 B1 | 10/2002 | Jago et al. | |
| 6,530,885 B1 | 3/2003 | Entrekin et al. | |
| 6,623,432 B2 | 9/2003 | Powers et al. | |
| 2008/0098816 A1* | 5/2008 | Yamashita | B06B 1/0629 73/596 |
| 2009/0062656 A1 | 3/2009 | Hyuga | |
| 2010/0262014 A1 | 10/2010 | Huang | |
| 2011/0034809 A1 | 2/2011 | Eberle et al. | |
| 2011/0088248 A1 | 4/2011 | Guo | |
| 2011/0181149 A1 | 7/2011 | Shikata | |
| 2011/0295124 A1* | 12/2011 | Shikata | B06B 1/064 600/459 |
| 2013/0172750 A1 | 7/2013 | Yoshimura et al. | |
| 2013/0223192 A1* | 8/2013 | Nishiwaki | H04B 11/00 367/135 |
| 2013/0257224 A1* | 10/2013 | Wodnicki | B06B 1/0622 310/319 |
| 2014/0132114 A1* | 5/2014 | Fukase | H01L 41/0475 310/322 |
| 2015/0097468 A1* | 4/2015 | Hajati | H01L 41/0825 310/334 |

FOREIGN PATENT DOCUMENTS

| | | |
|---|---|---|
| CN | 102755176 A | 10/2012 |
| JP | 2177944 A | 7/1990 |
| JP | 2010193072 A | 9/2010 |
| JP | 2013005403 A | 1/2013 |
| WO | 2004021404 A2 | 3/2004 |

OTHER PUBLICATIONS

Nikoozadeh, et al., "Forward-Looking Intracardiac Imaging Catheters Using Fully Integrated CMUT Arrays", http://www-kyg.stanford.edukhuriyakubopencmsDownloads10_Nikoozadeh_02.pdf (Abstract).

International Search Report and Written Opinion from International Application No. PCT/EP2015/059769, dated Jul. 13, 2015, 10 pages.

* cited by examiner

ULTRASONIC TRANSDUCER CHIP ASSEMBLY, ULTRASOUND PROBE, ULTRASONIC IMAGING SYSTEM AND ULTRASOUND ASSEMBLY AND PROBE MANUFACTURING METHODS

This application is the U.S. National Phase application under 35 U.S.C. § 371 of International Application No. PCT/EP2015/059769, filed on May 5, 2015, which claims the benefit of European Application Serial No. 14167101.6, filed May 6, 2014. These applications are hereby incorporated by reference herein.

FIELD OF THE INVENTION

The present invention relates to an ultrasonic transducer assembly including an ultrasonic transducer chip and a flexible interconnect to the ultrasonic transducer chip.

The present invention further relates to an ultrasound probe including such an ultrasonic transducer assembly.

The present invention yet further relates to an ultrasonic imaging system comprising such an ultrasound probe.

The present invention still further relates to a method of manufacturing such an ultrasonic transducer assembly.

The present invention still further relates to a method of manufacturing such an ultrasound probe.

BACKGROUND OF THE INVENTION

IC dies including ultrasound sensing capabilities, e.g. ultrasonic transducer chips, are increasingly used as a sensing tip of an ultrasound probe such as an ultrasound catheter. The ultrasound sensing capabilities may for instance be provided by a plurality of transducer elements in a main surface of the ultrasonic transducer chip, e.g. to provide a forward looking or sideward looking ultrasound probe. Popular technologies to implement the transducer elements include piezoelectric transducer elements formed of materials such as lead zirconate titanate (PZT) or polyvinylidene-fluoride (PVDF) and capacitive micro-machined ultrasonic transducer (CMUT) elements. An ultrasonic transducer chip based on such CMUT elements is sometimes referred to as a CMUT device.

CMUT devices are becoming increasingly popular because CMUT devices can offer excellent bandwidth and acoustic impedance characteristics, which makes them the preferable over e.g. piezoelectric transducers. Vibration of the CMUT membrane can be triggered by applying pressure (for example using ultrasound) or can be induced electrically. Electrical connection to the CMUT device, often by means of an integrated circuit (IC) such as an application specific integrated circuit (ASIC) facilitates both transmission and reception modes of the device. In reception mode, changes in the membrane position cause changes in electrical capacitance, which can be registered electronically. In transmission mode, applying an electrical signal causes vibration of the membrane.

A pressure causes a deflection of the membrane that is electronically sensed as a change of capacitance. A pressure reading can then be derived.

The ultrasonic transducer chip may be mounted on an epoxy backing block containing sound-absorbing heavy materials, as for instance is disclosed in US 2011/0088248 A1, in which the ultrasound probe further comprises a rigid printed circuit board (PCB) embedded in the backing block. However, it is rather cumbersome to manufacture such an ultrasound probe, as each probe has to be manufactured individually. Moreover, because the backing block encapsulates the PCB, the overall diameter of the ultrasound probe is increased, which is a disadvantage if the ultrasound probe is to be used to image small compartments, e.g. when used in cardiac imaging applications.

SUMMARY OF THE INVENTION

The present invention seeks to provide a compact ultrasonic transducer assembly that can be manufactured in a straightforward manner.

The present invention further seeks to provide an ultrasound probe including such an ultrasonic transducer assembly.

The present invention yet further seeks to provide an ultrasonic imaging system including such an ultrasound probe.

The present invention still further seeks to provide a method of manufacturing such an ultrasonic transducer assembly.

The present invention still further seeks to provide a method of manufacturing such an ultrasound probe.

According to an aspect, there is provided an ultrasonic transducer assembly comprising an ultrasonic transducer chip having a main surface comprising a plurality of ultrasound transducer elements and a plurality of first contacts for connecting to said ultrasound transducer elements; a contact chip having a further main surface comprising a plurality of second contacts for contacting a signal processing assembly; a backing member comprising ultrasound absorbing and/or scattering bodies, said backing member comprising a first surface on which the transducer chip is located and a second surface on which the contact chip is located; and a flexible interconnect extending over said backing member from the main surface to the further main surface, the flexible interconnect comprising a plurality of conductive tracks, each conductive track connecting one of said first contacts to a second contact.

Such an assembly facilitates high resolution ultrasound monitoring by suppressing reflected ultrasound waves interfering with the readings of the ultrasonic transducer chip due to the presence of the ultrasound scattering and/or absorbing backing member behind the ultrasonic transducer chip. In addition, the ultrasonic transducer assembly may be connected to a surface of a signal processing assembly such a carrier, e.g. a printed circuit board surface opposite the further main surface of the contact chip to form an ultrasound probe (tip). As these connections are located in between the carrier surface and the further main surface, such connections do not affect, i.e. increase, the outer diameter of the ultrasound probe, thereby providing a compact probe that can be used for investigations of small spaces, e.g. vascular or cardiac investigations when the ultrasound probe is used in a diagnostic setting. Moreover, the provision of contacts between a contact chip and an edge of a carrier facilitates a particularly straightforward assembly process of ultrasound probes as will be explained in more detail below.

The backing member may comprise a resin in which the ultrasound scattering and/or absorbing bodies are dispersed. For instance, the ultrasound scattering bodies may be hollow glass beads or other suitable body that can be used for ultrasound scattering. The ultrasound absorbing bodies may be bodies made of one or more heavy elements. For instance, the ultrasound absorbing bodies may be particles comprising tungsten, such as tungsten oxide particles.

In an embodiment, the flexible interconnect includes a first electrically insulating polymer layer and a second insulating polymer layer, wherein the conductive tracks are arranged in between said first and second electrically insulating polymer layers. The flexible interconnect may envelope the first contacts and the second contacts, e.g. to anchor the flexible interconnect on the respective surfaces of the ultrasonic transducer chip and the contact chip.

In an embodiment, the first surface may be opposite the second surface. Such an ultrasonic transducer assembly may for instance be used to provide a forward looking ultrasonic probe. Alternatively, the first surface may adjoin the second surface. Such an ultrasonic transducer assembly may for instance be used to provide a sideward looking ultrasonic probe.

The second contacts may be solder bumps and/or may define a ball grid array. This facilitates the connection of the contact chip to a signal processing assembly.

According to another aspect, there is provided an ultrasound probe comprising the ultrasonic transducer assembly according to one or more of the aforementioned embodiments and a signal processing assembly including a carrier carrying at least one signal processing circuit for processing signals from said transducer cells on a main carrier surface, said carrier comprising a further carrier surface adjoining the main carrier surface, the further carrier surface comprising a plurality of carrier contacts to said at least one signal processing circuit, wherein the carrier contacts are conductively coupled to the second contacts. Such an ultrasound probe benefits from a high resolution ultrasound imaging by the ultrasonic transducer chip due to the suppression of reflected or scattered ultrasound waves by the backing member and from a small form factor by the fact that the connections between the ultrasonic transducer assembly and the signal processing assembly are hidden in between opposing surfaces of these respective assemblies. Moreover, as the ultrasonic transducer assembly may be manufactured in a compact manner, an ultrasound probe having a relatively flexible tip may be provided.

The ultrasound probe may be included in an ultrasonic diagnostic system.

According to a further aspect, there is provided a method of manufacturing an ultrasonic transducer assembly, comprising providing a wafer including a first array of ultrasonic transducer chips, each having a main surface comprising a plurality of ultrasound transducer elements and a plurality of first contacts for connecting to said ultrasound transducer elements; a second array of contact chips, each having a further main surface comprising a plurality of second contacts for contacting a signal processing assembly; and a sacrificial region separating the first array from the second array; forming a flexible interconnect extending over said sacrificial region from the first contacts to the second contacts, the flexible interconnect comprising a plurality of conductive tracks, each conductive track connecting one of said first contacts to a second contact; removing the sacrificial region to release the first array and the second array; providing a backing material comprising ultrasound absorbing and/or scattering bodies; providing the first array on a first surface of said backing material; and providing the second array on a second surface of said backing material such that the flexible interconnect extends from the first array to the second array over said strip.

The provision of such an array of ultrasonic transducer assemblies facilitates the efficient manufacturing of ultrasound probes in a high-yield and cost effective manner, as singulation of the probes may be postponed until after the probes have been completed.

The step of forming the flexible interconnect may comprise forming a layer of a first flexible and electrically insulating material extending over said sacrificial region from the first contacts to the second contacts, said layer comprising a first plurality of openings exposing the first contacts and a second plurality of openings exposing the second contacts; forming a plurality of conductive tracks on said patterned layer, each of said conductive tracks being conductively coupled to one of said first contacts and to one of said second contacts; and optionally forming a further layer of a second flexible and electrically insulating material covering the first layer and the plurality of conductive tracks.

Such a flexible interconnect may electrically insulate the first contacts and second contacts whilst joining the ultrasonic transducer chips and the contact chips together. This further simplifies the manufacture of the ultrasonic transducer assemblies.

The thus manufactured ultrasonic transducer assemblies may be provided in a method of manufacturing an ultrasound probe, the method further comprising providing a signal processing assembly including a plurality of carriers, each carrier comprising a main carrier surface for carrying at least one signal processing circuit for processing signals from said transducer cells; and a further carrier surface adjoining the main carrier surface, the further carrier surface comprising a plurality of carrier contacts for connecting to said at least one signal processing circuit; forming an assembly of ultrasound probes by coupling each of the second contacts to a respective carrier contact; and singulating the ultrasound probes.

This facilitates a cost-effective and high yield manufacturing process of such ultrasound probes, as singulation of the probes is postponed until after the signal processing assemblies are connected to the ultrasonic transducer assemblies. Specifically, the formation of these connections becomes less cumbersome because of the improved stability provided by the respective assemblies being connected to each other whilst still forming part of an array of such assemblies.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

It should be understood that the Figures are merely schematic and are not drawn to scale. It should also be understood that the same reference numerals are used throughout the Figures to indicate the same or similar parts.

Figure 1:
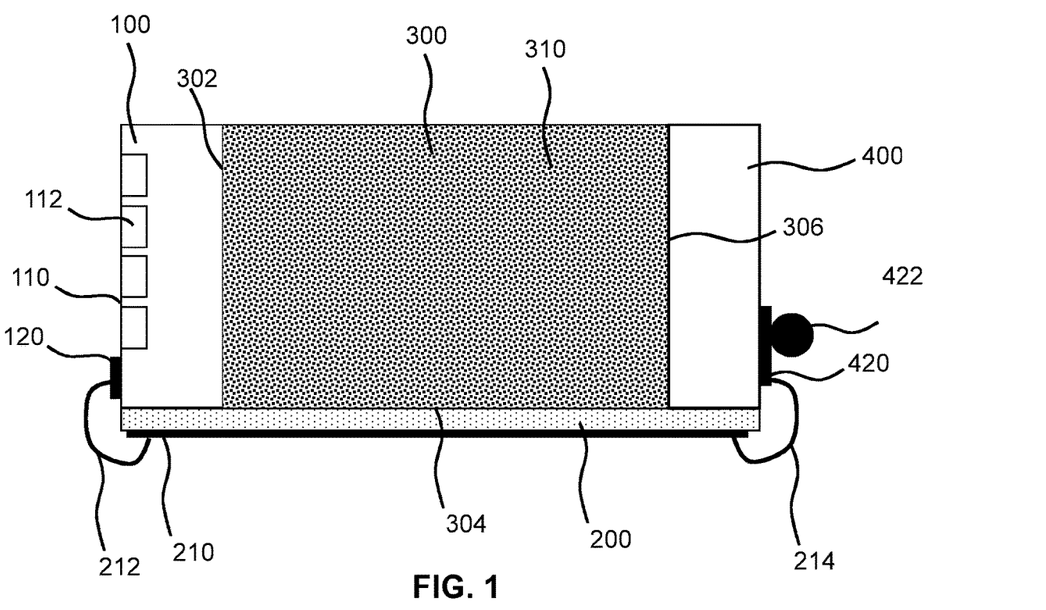
FIG. 1 schematically depicts an ultrasonic transducer assembly according to an embodiment of the present invention.

FIG. 1 schematically depicts an ultrasonic transducer assembly according to an embodiment of the present invention. The assembly comprises an ultrasonic transducer chip 100 having a major surface comprising an ultrasound transducer area 110, which typically comprises a plurality of transducer elements 112, such as CMUT or PZT elements. In a preferred embodiment, the major surface comprises an ultrasound transducer area 110 formed by a plurality of CMUT elements 112. The major surface further comprises a plurality of contacts 120, which may provide points of contact to the transducer elements 112 in any suitable manner as is well-known per se. Any suitable embodiment of such a transducer chip 100 may be chosen; it should be understood that embodiments of the present invention are not limited to a particular embodiment of such a transducer chip. For instance, the transducer chip 100 may be realized in any suitable semiconductor technology, e.g. CMOS, BiCMOS, bipolar technology and so on, using any suitable semiconductor substrate material, e.g. silicon, silicon-on-insulator, SiGe, GaAs and so on.

The ultrasonic transducer chip 100 is typically mounted, e.g. an adhered, onto a first surface 302 of a backing member 300. The backing member 300 typically comprises a resin such as an epoxy resin in which ultrasound scattering and/or absorbing bodies 310 are included. For instance, the ultrasound scattering bodies 310 and/or ultrasound absorbing bodies 310 may be dispersed in the resin. Such bodies 310 suppress or even prevent scattered and/or reflected ultrasound waves from reaching the ultrasonic transducer elements 112 of the ultrasonic transducer chip 100. This may improve the resolution of the ultrasound image generated by the ultrasonic transducer chip 100, as predominantly or only ultrasound waves generated and reflected in the intended direction (e.g. forward generated and reflected ultrasound waves in the case of a forward-looking ultrasound probe including the ultrasonic transducer chip 100) are detected by the ultrasonic transducer elements 112 of the ultrasonic transducer chip 100. In other words, the suppression or prevention of ultrasound waves from other directions reaching the ultrasonic transducer chip 100 by the backing member 300 reduces or even avoids interference from such stray ultrasound waves with the ultrasound waves from the direction of interest.

Any suitable ultrasound scattering materials may be used to form the ultrasound scattering bodies 310 in the backing member 300. For instance, a non-limiting example of such an ultrasound scattering body 310 is a hollow glass sphere although other suitable ultrasound scattering bodies will be immediately apparent to the skilled person. Similarly, any suitable solid materials may be used to form the ultrasound absorbing bodies 310. It is well-known per se that heavy materials, e.g. materials based on heavy metals, are ideally suited for such a purpose. A non-limiting example of such a material is tungsten. For instance, the ultrasound absorbing bodies may comprise tungsten, such as in the form of tungsten oxide. Again, it will be immediately apparent to the skilled person that many suitable alternatives to tungsten are readily available, and such suitable alternatives are equally feasible to be used in the backing member 300.

The ultrasonic transducer assembly further comprises a contact chip 400 mounted on, e.g. adhered to, a further surface 306 of the backing member 300. The contact chip 400 typically comprises a plurality of second contacts 420 for establishing a connection with a signal processing assembly as will be explained in more detail later. Any suitable embodiment of such a contact chip 400 may be chosen; it should be understood that embodiments of the present invention are not limited to a particular embodiment of such a contact chip. For instance, the contact chip 400 may be realized in any suitable semiconductor technology, e.g. CMOS, BiCMOS, bipolar technology and so on, using any suitable semiconductor substrate material, e.g. silicon, silicon-on-insulator, SiGe, GaAs and so on.

Second contacts 420 may be realized in any suitable electrically conductive material, such as any material that is commonly used for the formation of such contacts, e.g. any suitable metal or metal alloy. In an embodiment, the second contacts 420 carry a solder bump 422 for establishing the electrical connection with the signal processing assembly.

The ultrasonic transducer assembly further comprises a flexible interconnect 200 including a plurality of conductive tracks 210 for establishing an electrically conductive connection between the first contacts 120 of the ultrasonic transducer chip 100 and the second contacts 420 of the contact chip 400. In FIG. 1, the flexible interconnect extends over a further surface 304 of the backing member 300. Such a flexible interconnect 200 may for instance be formed of an electrically insulating flexible polymer such as polyimide, wherein the conductive tracks 210 may be formed by depositing a metal layer such as a copper layer over the electrically insulating flexible polymer and patterning the metal layer to form the conductive tracks 210. In an embodiment, the flexible interconnect 200 may be a Flex foil or a copper-coated polyimide such as a Pyralux® foil as marketed by the Du Pont company In the embodiment shown in FIG. 1, each conductive tracks 210 is connected to a first contact 120 by a first bond wire 212 and is connected to a second contact 420 by a second bond wire 214. It is emphasised that these collections are by way of a non-limited example only and that the conductive tracks 210 may be connected to the first contacts 120 and the second contacts 420 in any suitable manner.

In the embodiment shown in FIG. 1, the ultrasonic transducer chip 100 and the contact chip 400 may be discretely manufactured chips, e.g. chips manufactured in different manufacturing processes using different technologies, which chips are interconnected to each other by the flexible interconnect 200 after singulation. This has the advantage of increased flexibility in the designs of the ultrasonic transducer chips 100 and the contact chips 400, but comes at the cost of a more involved assembly process of the ultrasonic producer assembly, as it can be cumbersome to connect the flexible interconnect to the respective chips.

Figure 2:
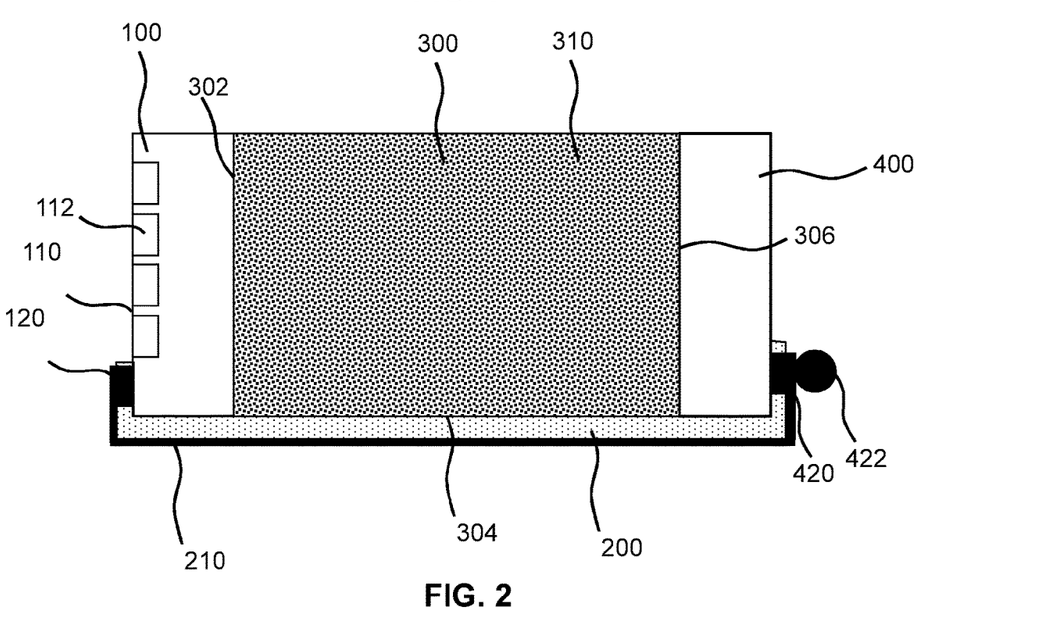
FIG. 2 schematically depicts an ultrasonic transducer assembly according to another embodiment of the present invention.

FIG. 2 schematically depicts an alternative embodiment of an ultrasonic transducer assembly, in which the ultrasonic transducer chip 100, the contact chip 400 and the flexible interconnect 200 are produced in a single production process, as will be explained in more detail later on with the aid of FIG. 4.

In this embodiment, the flexible interconnect 200 is affixed to and/or anchored on the major surface of the ultrasonic transducer chip 100 and the major surface of the contact chip 400. In an embodiment, the flexible interconnect 200 may envelope the first contacts 120 and/or the second contacts 420. The flexible interconnect 200 may comprise first openings exposing the first contacts 120 and/or second openings exposing the second contacts 420. In an embodiment, the first contacts 120 may be covered by the flexible interconnect 200 to electrically insulate the first contacts 120, whereas the second contacts 420 may be exposed by openings in the flexible interconnect 200.

As shown in FIG. 2, the flexible interconnect 200 may comprise a first electrically insulating flexible polymer layer covered by the conductive tracks 210, such that the conductive tracks 210 are exposed. In an alternative embodiment, which will be described in more detail with the aid of FIG. 4, the flexible interconnect 200 may comprise a second electrically insulating flexible polymer layer covering the first electrically insulating flexible polymer layer and the conductive tracks 210, such that the conductive tracks 210 are sandwiched in between the first and second electrically insulating flexible polymer layers. This has the advantage that the conductive tracks are electrically insulated from the surroundings of the ultrasonic transducer assembly, such as bodily fluids, e.g. blood when the ultrasonic transducer assembly is used as part of an ultrasound probe tip for invasive diagnostic investigations of a patient's body.

Figure 3:
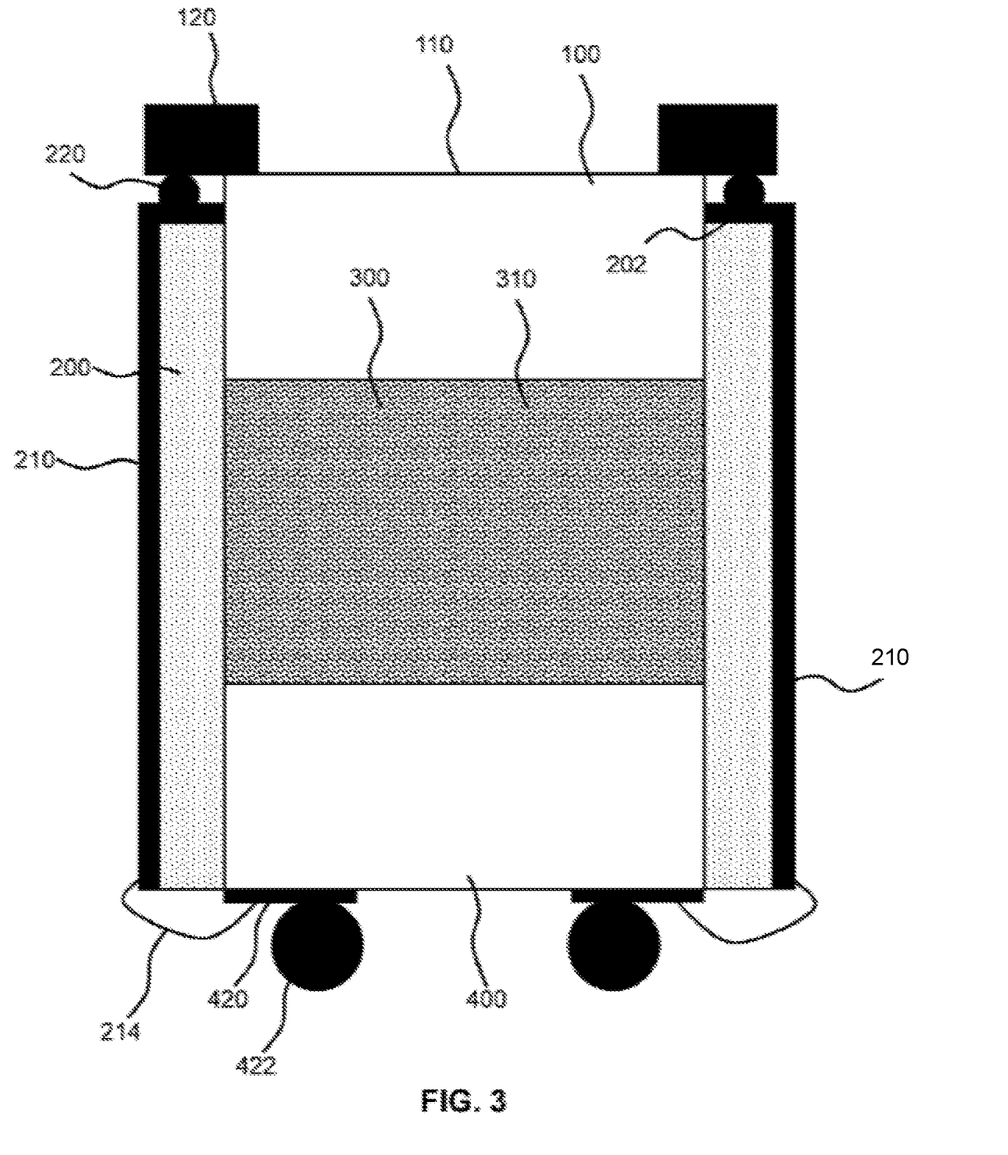
FIG. 3 schematically depicts an ultrasonic transducer assembly according to yet another embodiment of the present invention.

FIG. 3 schematically depicts yet another example embodiment of an ultrasonic transducer assembly in which the ultrasonic transducer chip 100 is mounted on a first surface of the backing member 300 and is interconnected to a contact chip 400 on a second surface of the backing member 300 by a flexible interconnect 200. In this embodiment, an edge portion 202 of the flexible interconnect 200 is also covered by the interconnect 210, which edge portion 202 is conductively coupled to a first contact 120 extending beyond the perimeter of the ultrasonic transducer chip 100 using a solder 220. This for instance is advantageous if the ultrasonic transducer chip 100 is a circular chip, and the flexible interconnect 200 defines a cylindrical holder of the ultrasonic transducer chip 100, i.e. the ultrasonic transducer chip 100 is recessed in a cavity delimited by the flexible interconnect 200 and the backing member 300. The conductive tracks 210 may be formed on the edge portion 202 of the flexible interconnect 200 using plating techniques. Similarly, the first contact 120 may be made to extend beyond the perimeter of the ultrasonic transducer chip 100 by plating an electrically conductive material on the chip contacts prior to release of the chip from its wafer, wherein the plated material extends beyond the chip boundary. This allows for the ultrasonic transducer chip 100 to be suspended in a cavity by the first contacts 120. This embodiment has the advantage that a ultrasonic transducer assembly having a particular compact outer diameter can be achieved.

In FIG. 3, the conductive tracks 210 are connected to the second contacts 420 of the contact chip 400 using wire bonds 214 by way of non-limiting example only. It should be understood that it is equally feasible that the flexible interconnect 200 extends over part of the major surface of the contact chip 400 to provide the type of contacts as shown in FIG. 2, e.g. wherein the flexible interconnect 200 envelopes the second contacts 420 and comprises openings through which the second contacts 420 are exposed.

At this point, it is noted that FIG. 1-3 depict example embodiments of ultrasonic transducer assemblies, highlighting examples of suitable connections between the ultrasonic transducer chip 100 and the contact chip 400 on the one hand and the flexible interconnect 200 on the other hand. It is reiterated that the present invention is not limited to these specific examples and that any suitable connection between such chips and the flexible interconnect 200 may be contemplated, as long as a contact chip 400 is provided at the backing member 300 that facilitates the connection of the ultrasonic transducer assembly to an edge surface of a carrier such as a printed circuit board (PCB) forming part of a signal processing assembly, as will be explained in more detail below.

In the context of the present invention, an ultrasonic transducer chip 100 may, in addition to the transducer elements 112 in the transducer area 110 and the first contacts 120, further include passive as well as active components, and may have any suitable functionality, e.g. sensor devices, signal processing circuits, and so on. Similarly, the contact chip 400, in addition to the second contacts 420 for contacting with carrier contacts on a carrier edge, may further include passive as well as active components, and may have any suitable functionality, e.g. sensor devices, signal processing circuits, and so on although this is of course not essential.

It is furthermore noted that in the embodiments shown in FIG. 1-3, the ultrasonic transducer chip 100 and the contact chip 400 are mounted on opposite surfaces of the backing member 300 by way of non-limiting example. This arrangement for instance is suitable for use as a tip of a forward-looking ultrasound probe. However, it is equally feasible to mount the ultrasonic transducer chip 100 on a surface of the backing member 300 that adjoins the second surface 306 onto which the contact chip 400 is mounted. Such an arrangement for instance is suitable for use as a tip of a sideways-looking ultrasound probe.

The ultrasonic transducer assembly may further comprise additional ultrasonic transducer chips 100 to increase the directionality of the imaging capability of the ultrasonic transducer assembly when used as the tip of an ultrasound probe. For instance, a first ultrasonic transducer chip 100 may be mounted on the first surface 302 of the backing member 300, and at least one additional ultrasonic transducer chip 100 may be mounted on one or more of the surfaces of the backing member 300 that extend from the first surface 302 to the second surface 306 of the backing member 300 to provide an ultrasonic transducer assembly that can be used as a forward and sideways-looking probe tip of an ultrasound probe. Alternatively, the ultrasonic transducer assembly may comprise a plurality of ultrasound transducer chips mounted on respective surfaces of the backing member 300 that adjoin the surface 306 on which the contact chip 400 is mounted in order to provide an ultrasonic transducer assembly that can be used as a multi-directional sideways-looking probe tip of an ultrasound probe. Other variations will be immediately apparent to the skilled person.

In a particularly advantageous embodiment, the ultrasonic transducer assembly is formed as an array of such assemblies, which may be connected to an array of signal processing assemblies prior to singulation, such that a plurality of ultrasound probes may be formed in a highly efficient and cost-effective manner, because individual probes do not have to be assembled individually, which simplifies the manufacturing process of such probes.

Figure 4:
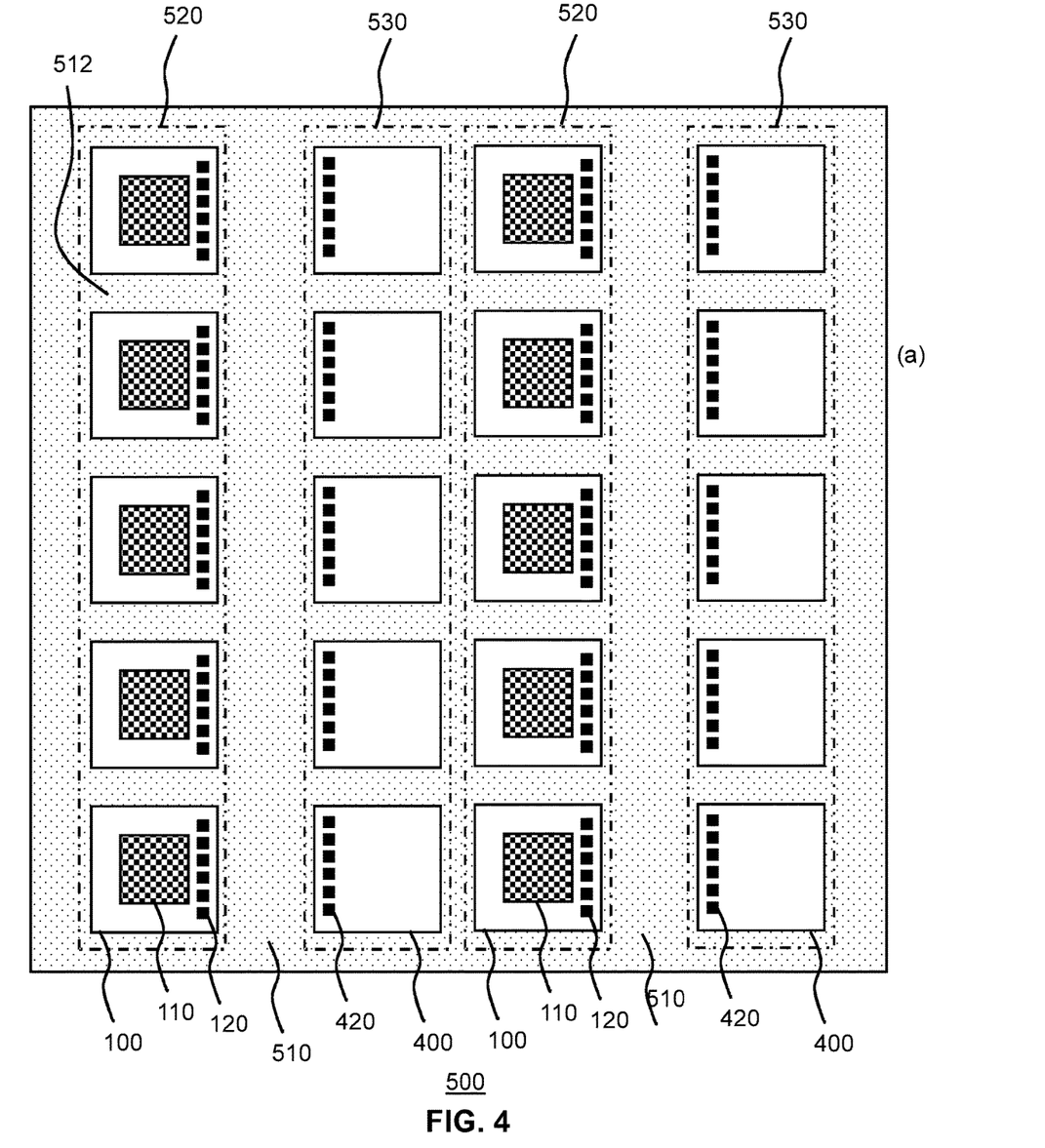
FIG. 4 schematically depicts a method of manufacturing an array of ultrasonic transducer assemblies of FIG. 2.

In FIG. 4, a non-limiting example of a method in accordance with an embodiment of the present invention is schematically depicted in which such an assembly array is formed. In a first step, depicted in FIG. 4(a), a wafer 500 is provided in which a plurality of ultrasonic transducer chips 100 have been formed in one or more arrays 520 and in which contact chips 400 including second contacts 420 are formed in one or more arrays 530 (two arrays 520, 530 are shown by way of non-limiting example). The arrays 520 of the ultrasonic transducer chips 100 are separated from a neighbouring array 530 of the contact chips 400 by a sacrificial region 510 of the wafer 500. Individual chips within each of the arrays 520, 530 are separated by a further sacrificial wafer region 512, e.g. a scribe line or the like as will be explained in more detail later.

As mentioned before, the wafer 500 may be any suitable wafer, such as a silicon wafer, a silicon-on-insulator wafer or a wafer of other suitable semiconductor materials. In an embodiment, the wafer 10 may comprise an etch stop layer 12, such as an oxide layer. Its purpose will be explained in more detail later. The first contacts 120 of each ultrasonic transducer chip 100 are to be connected to the second contacts 420 of an opposing contact chip 400 by a flexible interconnect 200 extending across the sacrificial region 510. Such a flexible contact extension can be seen as a microscopic version of a flat cable, which use is well-known at the printed circuit board (PCB) level.

The method proceeds as shown in FIG. 4(*b*) with the provision of a layer of a flexible and electrically insulating material 200 on the front side of the wafer 500, which is subsequently patterned by photolithography to expose the first and second contacts 120, 420 underneath the layer 200. Any suitable material may be used for the layer 200. The flexible and electrically insulating material may be chosen from the group consisting of parylene, polyimide, polyimide resins, polycarbonate, fluorocarbon, polysulphon, epoxide, phenol, melamine, polyester, and silicone resins or their co-polymers. Polyimide and parylene are particularly suitable when the IC is to be integrated into an invasive medical device as these materials have been cleared for use in invasive medical devices.

The thickness of the layer of a flexible and electrically insulating material 200 preferably is selected in the range from 1-20 μm and more preferably in the range of 1-10 μm to ensure that the resultant has sufficient flexibility. If the layer 200 becomes too thick, its flexibility will be reduced. However, if the layer 200 becomes too thin, it may be damaged too easily.

In a subsequent step, shown in FIG. 4(*c*), a conductive material is deposited on the layer of the flexible and electrically insulating material 200 and subsequently patterned to provide respective conductive tracks 210 in conductive contact with the exposed first and second contacts 120, 420 underneath the layer 200. Any suitable electrically conductive material, such as Al, Cu or other suitable metals and metal alloys may be used.

In an optional step shown in FIG. 4(*d*), The conductive tracks 22 are subsequently covered with a second layer of a flexible and electrically insulating material 200', which preferably is the same material as used for layer 200, although this is not essential. In other words, the materials used for layers 200 and 200' respectively may be individually selected from the previously described group of suitable compounds.

In a preferred embodiment, layers 200 and 200' are made of the same material, e.g. polyimide or parylene, and have the same thickness, e.g. approximately 5 μm. By using the same thickness for both layers 200 and 200', the conductive track(s) 210 are situated at the so called neutral line of stress of the flexible contact extension of the contacts 14.

If present, the second layer 200' of a flexible and electrically insulating material may be covered with a thin protective layer (not shown) from subsequent wafer processing steps. Any suitable material, such as a metal, e.g. Al may be used. The use of a material that can serve both to protect the layer 200' during the subsequent processing steps as well as a hard-etch mask for the subsequent patterning of the second layer of a flexible and electrically insulating material 24 is preferred as it reduces the wafer processing complexity. For this reason, metals such as Al are preferred.

As shown in FIG. 4(*e*), the method proceeds by applying and patterning a resist layer 502 on the backside of the wafer 500. Alternatively the resist layer 502 may be replaced by a patterned hard mask. The patterned resist layer 502, which may be any suitable material including a similar or the same material used for the previously mentioned thin protective layer over the second layer 200', protects (covers) the areas of the arrays 520, 530 in the wafer 500.

In a next step, shown in FIG. 4(*f*), the exposed parts of the back-side of the wafer 500, i.e. the parts not covered by the patterned resist 502 are exposed to an etch recipe, preferably an anisotropic etch recipe such as the Bosch process, for instance in case of the wafer 500 being a silicon wafer, with the exposed parts being etched to a depth corresponding to the intended final thickness of the chips 100, 400 to be formed from the wafer 500, to release (singulate) the arrays 520, 530, with each array 520 connected to an array 530 by the flexible interconnect 200. It is noted that the Bosch process, which typically comprises consecutive etching and passivation steps, is well-known per se, and will therefore not be explained in further detail for reasons of brevity only. Other suitable etch recipes of course may also be contemplated. The patterned resist 502 is subsequently stripped from the backside of the wafer 500.

Finally, as shown in step (g), the ultrasonic transducer assembly is completed by wrapping the first array 520, flexible interconnect 200 and second array 530 over a strip of backing members 300, wherein the first array may be adhered to a first surface of the strip by a first adhesive 522 and the second array may be adhered to a second surface of the strip by a second adhesive 532. The first adhesive 522 and the second adhesive 532 may be the same or may be different adhesives. Suitable adhesives include but are not limited to Epotek 301® as marketed by Epoxy Technology, Inc. from Billerica, Mass., USA or other suitable two-component epoxy-based adhesives.

At this point it is noted that the solder bumps 422 may be formed on the second contacts 420 at any suitable point in the aforementioned manufacturing process, for instance before or after the singulation of the arrays 520, 530. The solder bumps 422 may be formed on the contacts 420 in any suitable manner, for instance by using a laser process as available from the PacTech Company, Nauen, Germany.

At this point it is also noted that the backing member 300 may be formed in between the first array 520 and the second array 530 in any suitable manner. For instance, as an alternative to step (g), the backing member 300 including the ultrasound scattering and/or absorbing bodies 310 dispensed therein may be poured in a liquid or fluid form in between the first array 520 and the second array 530 after which the backing member 300 is solidified, e.g. through cooling or curing in order to form the ultrasonic transducer assembly array. To this end, the first array 510 and the second array 520 may be placed in a holder, thereby forming a space to be occupied by the backing member 300. This space is subsequently filled with the backing material 300 in fluid or liquid form. The holder is typically removed once the backing material 300 has been solidified. In this embodiment, no adhesives need to be used to mount the first array 520 and the second array 530 on the respective surfaces of the backing member 300.

Figure 5:
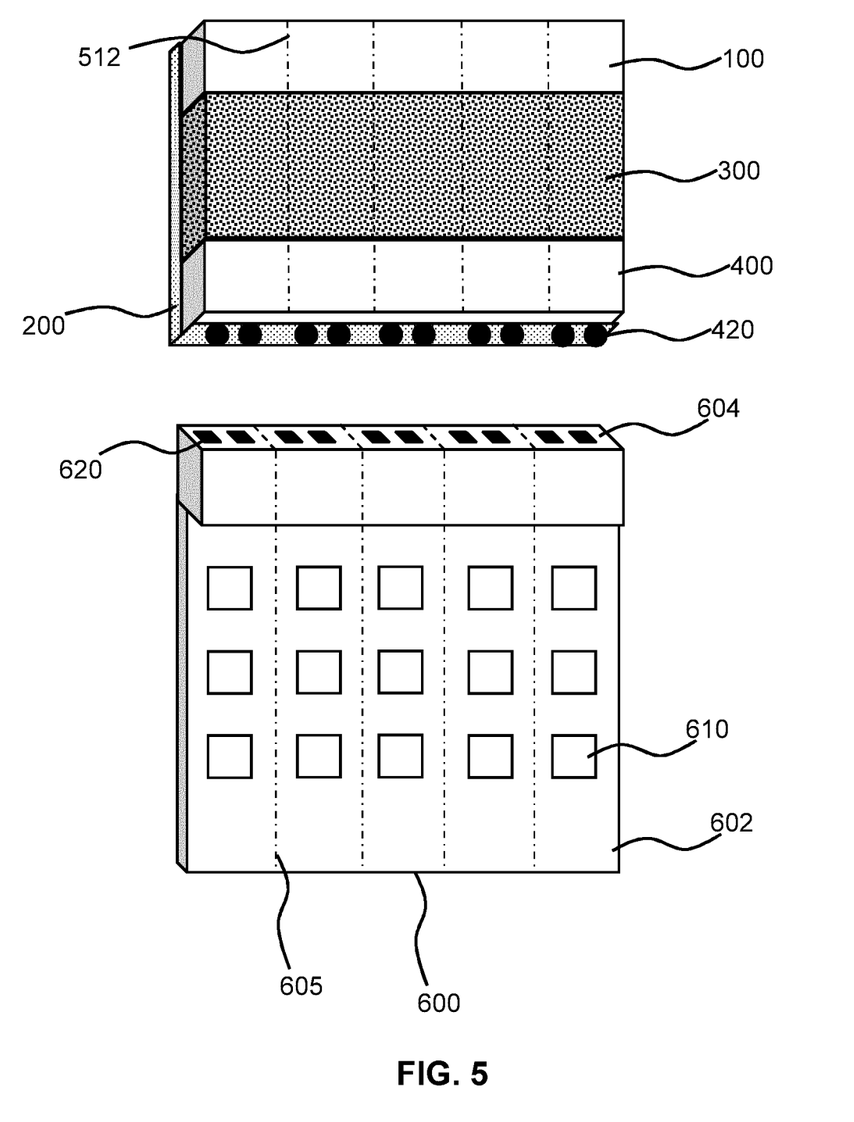
FIG. 5 schematically depicts a method of manufacturing an ultrasound probe assembly using the array of ultrasonic transducer assemblies as manufactured by the method depicted in FIG. 4.

The resulting array of ultrasonic transducer assemblies is shown in FIG. 5 together with an array of signal processing assemblies including an array of carriers 600, e.g. PCBs, having a first surface 602 onto which one or more signal processing elements 610 for processing signals generated by the ultrasonic transducer chips 100 are mounted, e.g. one or more signal processing circuits as will be explained in more detail below. The carriers 600 further comprise a second surface 604 adjoining the first surface 602, which second surface 604 may be an edge surface such as a leading edge surface of the carrier 600. In an embodiment, the carrier 600 may have a first thickness in the region carrying the one or more signal processing elements 610 and a second thickness in the region including the second surface 604, the second thickness of being larger than the first thickness. For instance, the carrier 600 may comprise a bulging portion proximal to the contact chip 400 in order to increase the area of the second surface 604, in order to facilitate the provision of the required number of carrier contacts 620 at the required pitch on the second surface 604.

Each second surface 604 typically carries a plurality of carrier contacts 620 arranged in a pattern and pitch that matches the pattern and pitch of the second contacts 420 on the respective contact chips 400. Consequently, an ultrasound probe assembly may be manufactured by mating the second contacts 420 on the contact chips 400 with corresponding carrier contacts 620 on the respective second surfaces 604 of the carriers 600. For instance, the second contacts 420 may comprise solder balls 422 as previously explained, which solder balls may be melted to establish the connections between the second contacts 420 and the carrier contacts 620. Other suitable ways of establishing such connections between the respective contacts will be immediately apparent to the skilled person and are not explained in further detail for the sake of brevity only. As previously explained, because the electrically conductive connection between the ultrasonic transducer assembly and a signal processing assembly is formed in between opposing surfaces of the contact chip 400 on the one hand and the edge surface 604 of the carrier 600 on the other hand, a particularly compact interconnect structure is achieved, which aids the miniaturization, i.e. the reduction of the outer diameter, of an ultrasound probe formed by the assembled ultrasonic transducer assembly and signal processing assembly.

Moreover, because the ultrasonic transducer assemblies and the signal processing assemblies are not individualized prior to forming the interconnection between the respective assemblies, a more straightforward ultrasound probe assembly process is achieved, because the arrays of ultrasonic transducer assemblies and signal processing assemblies can be handled more easily than individual assemblies. Individualization of the ultrasound probes may be achieved after combining the aforementioned assembly arrays, with individual ultrasonic transducer assemblies being delimited from each other as indicated by the dashed line 512 and individual signal processing assemblies being delimited from each other as indicated by the dashed line 605. The dashed lines 512, 605 for instance may indicate scribe lines or other suitable delineations of components to be individualized, as is well-known per se in the art.

Figure 6:
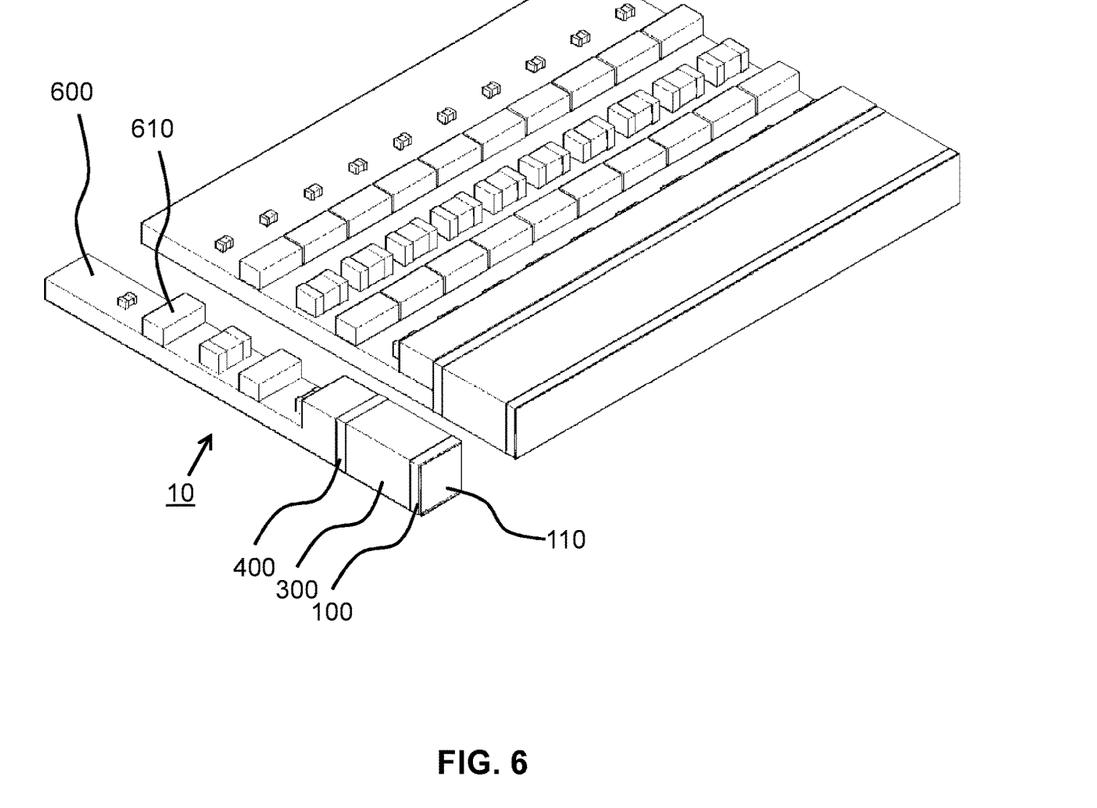
FIG. 6 schematically depicts the formation of individual ultrasound probes from an ultrasound probe assembly according to an embodiment of the present invention.

This is shown in more detail in FIG. 6, in which an ultrasound probe 10 is formed by individualizing the probe 10 along the dashed lines 512, 605, e.g. by (laser) cutting, sawing, dicing or the like, which techniques are well-known per se for individualizing components, e.g. individualizing chips on a wafer, such that these techniques will not be explained in further detail for the sake of brevity only. Consequently, individualized ultrasound probes may be achieved that each comprise an ultrasonic transducer chip 100 comprising a transducer area 110, which ultrasonic transducer chip 100 is mounted onto a backing member 300 including ultrasound wave scattering and/or absorbing materials as previously explained. The backing member 300 further carries a contact chip 400 connected to a signal processing assembly including a carrier 600 such as a PCB, which carries one or more signal processing elements 610, e.g. one or more signal processing circuits. The interconnections between the contact chip 400 and the carrier 600 are located in between the edge surface of the carrier 600 facing the contact chip 400 and the main surface of the contact chip 400 facing this edge surface.

Although not specifically shown, the ultrasound probe 10 may further comprise a tubular body onto which the assembly shown in FIG. 6 may be mounted. Such a tubular body may be any suitable tubular body, which may house one or more wires or cables for connecting the signal processing assembly of the ultrasound probe 10 to a diagnostic control unit. This is entirely conventional, and will therefore not be explained in further detail for the sake of brevity only.

Figure 7:
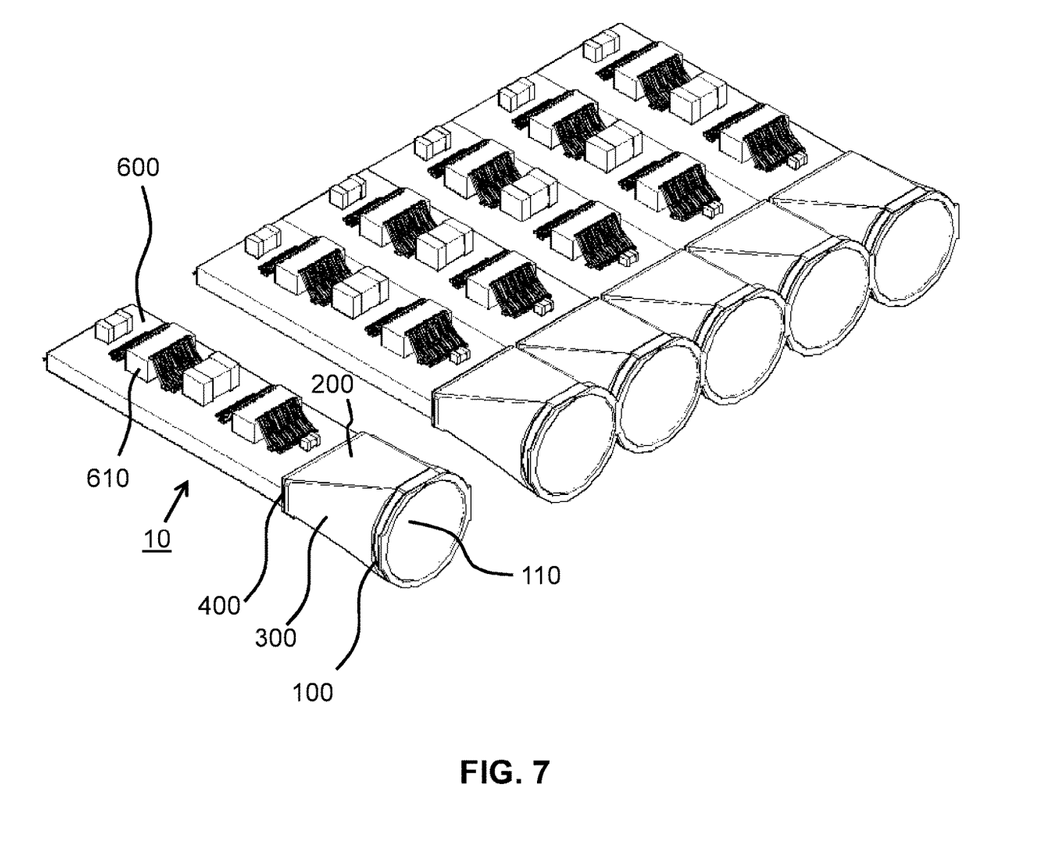
FIG. 7 schematically depicts the formation of individual ultrasound probes from an ultrasound probe assembly according to another embodiment of the present invention.

In the embodiments described so far, the ultrasonic transducer chip 100 and the contact chip 400 have been depicted as oblong chips. It should be understood that this is by way of non-limiting example only as each of these chips may have any suitable shape. In particular, the ultrasonic transducer chips 100 may have a circular shape, which shape for instance may be readily achieved by the aforementioned Bosch process as is well-known per se. FIG. 7 schematically depicts a singulation process in which ultrasound probes 10 having such a circular ultrasonic transducer chip 100 connected to a contact chip 400 by the flexible interconnect 200 extending over the backing member 300 are formed after an array of such ultrasonic transducer assemblies has been assembled onto an array of signal processing assemblies including carriers 600 carrying one or more signal processing elements 610 connected to contact chips 400 as previously explained. It will be understood that in this embodiment the shape of the backing member 300 may be adjusted in accordance with the shape of the ultrasonic transducer chip 100. The contact chip 400 may also have a circular shape although it may be advantageous for the contact chip 400 to have an oblong, e.g. rectangular or square, shape to more easily match the shape of the edge surface of the carrier 600 that carries the carrier contacts 620.

It is reiterated that in the above embodiments the ultrasound probes 10 are forward looking ultrasound probes by way of non-limiting example only. It is equally feasible to provide one or more ultrasonic transducer chips 100 on the side surfaces of the backing member 300, i.e. on a surface adjoining the surface onto which the contact chip 400 is mounted to provide a sideward looking ultrasound probe 10. Such sideward looking ultrasonic transducer chips 100 may be included in addition to or as an alternative to the forward-looking ultrasonic transducer chip 100 explicitly shown in the aforementioned embodiments.

It is furthermore noted at this point that although FIG. 5 schematically depicts a manufacturing method in which the flexible interconnect 200 is formed prior to singulating the first arrays 520 and the second arrays 530, it is of course equally feasible to form the flexible interconnect 200 after the arrays have been singulated, for instance to form ultrasonic transducer assemblies as shown in FIGS. 1 and 3. As the connection of a flexible interconnect to such chips is well-known per se, this will not be explained in further detail for the sake of brevity only.

Figure 8:
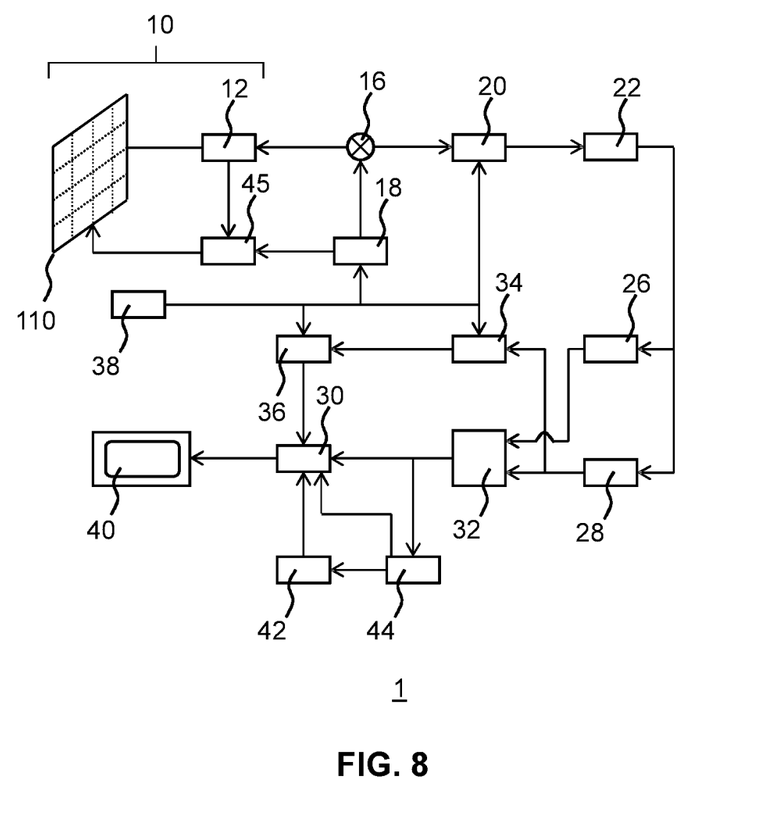
FIG. 8 schematically depicts an ultrasound imaging system according to an embodiment of the present invention.

Referring to FIG. 8, an example embodiment of an ultrasonic diagnostic imaging system with an array transducer probe according to an embodiment of the present invention is shown in block diagram form. In FIG. 8 a CMUT transducer array 110 on an ultrasound transducer chip 100 (not shown in FIG. 10) is provided in an ultrasound probe 10 for transmitting ultrasonic waves and receiving echo information. The transducer array 110 may alternatively comprise piezoelectric transducer elements formed of materials such as lead zirconate titanate (PZT) or polyvinylidenefluoride (PVDF). The transducer array 110 may be a one- or a two-dimensional array of transducer elements capable of scanning in a 2D plane or in three dimensions for 3D imaging.

The transducer array 110 is coupled to a microbeam former 12 in the probe 10 which controls transmission and reception of signals by the CMUT array cells or piezoelectric elements. Microbeam formers are capable of at least partial beam forming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The microbeam former 12 is coupled by the probe cable, e.g. coaxial cable 410, to a transmit/receive (T/R) switch 16 which switches between transmission and reception and protects the main beam former 20 from high energy transmit signals when a microbeam former is not present or used and the transducer array 110 is operated directly by the main system beam former 20. The transmission of ultrasonic beams from the transducer array 110 under control of the microbeam former 12 is directed by a transducer controller 18 coupled to the microbeam former by the T/R switch 16 and the main system beam former 20, which receives input from the user's operation of the user interface or control panel 38. One of the functions controlled by the transducer controller 18 is the direction in which beams are steered and focused. Beams may be steered straight ahead from (orthogonal to) the transducer array 110, or at different angles for a wider field of view. The transducer controller 18 may be coupled to control a DC bias control 45 for the CMUT array. For instance, the DC bias control 45 sets DC bias voltage(s) that are applied to the CMUT cells 150 of a CMUT array 110.

The partially beam-formed signals produced by the microbeam former 12 are forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of CMUT transducer cells 112 (see FIG. 1-3) or piezoelectric elements. In this way the signals received by thousands of transducer elements of a transducer array 110 can contribute efficiently to a single beam-formed signal.

The beam-formed signals are coupled to a signal processor 22. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 26 and optionally to a Doppler processor 28. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.)

The 2D or 3D images are coupled from the scan converter 32, multiplanar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 110 and hence the images produced by the transducer array and the ultrasound system. The user interface is also coupled to the multiplanar reformatter 44 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the microbeam former 12 and/or the Doppler processor 28 may be omitted, the ultrasound probe 10 may not have 3D imaging capabilities and so on. Other variations will be apparent to the skilled person.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasonic transducer assembly comprising:
   an ultrasonic transducer chip having a main surface comprising a plurality of CMUT ultrasound transducer elements and a plurality of first contacts for connecting to said CMUT ultrasound transducer elements;
   a single contact chip having a further main surface comprising a plurality of second contacts for contacting a signal processing assembly;
   a backing member comprising ultrasound absorbing and/or scattering bodies, said backing member comprising a first surface on which the transducer chip is located and a second surface on which the contact chip is located; and
   a flexible interconnect in contact with, and extending over a third surface of said backing member from the main surface to the further main surface, the flexible interconnect comprising a plurality of conductive tracks, each conductive track connecting one of said first contacts to a second contact.

2. The ultrasonic transducer assembly of claim 1, wherein the backing member comprises a resin in which the ultrasound scattering and/or absorbing bodies are dispersed.

3. The ultrasonic transducer assembly of claim 1, wherein the ultrasound scattering members are hollow glass beads and/or the ultrasound absorbing members are particles comprising tungsten, such as tungsten oxide particles.

4. The ultrasonic transducer assembly of claim 1, wherein the flexible interconnect includes a first electrically insulating polymer layer and a second insulating polymer layer, wherein the conductive tracks are arranged in between said first and second electrically insulating polymer layers.

5. The ultrasonic transducer assembly of claim 1, wherein the first surface is opposite the second surface.

6. The ultrasonic transducer assembly of claim 1, wherein the first surface adjoins the second surface.

7. The ultrasonic transducer assembly of claim 1, wherein the second contacts comprise solder bumps.

8. The ultrasonic transducer assembly of claim 1, wherein the second contacts define a ball grid array.

9. The ultrasonic transducer assembly of claim 1, wherein the flexible interconnect envelopes the first contacts and the second contacts.

10. An ultrasound probe comprising:
    the ultrasonic transducer assembly of claim 1; and
    a signal processing assembly including a carrier carrying at least one signal processing circuit on a main carrier surface for processing signals from said transducer elements, said carrier comprising a further carrier surface adjoining the main carrier surface, the further carrier surface comprising a plurality of carrier contacts to said at least one signal processing circuit, wherein the carrier contacts are conductively coupled to the second contacts.

11. The ultrasound probe of claim 10, wherein the further carrier surface is an edge surface of the carrier.

12. An ultrasonic imaging system including the ultrasound probe of claim 10.

* * * * *